United States Patent

Chen et al.

[11] Patent Number: 5,869,721
[45] Date of Patent: Feb. 9, 1999

[54] BIDENTATE COORDINATED TRIVALENT GROUP IVB METAL COMPLEX CATALYST FOR PREPARING SYNDIOTACTIC VINYL AROMATIC POLYMER

[75] Inventors: Yi-Chun Chen, Taichung; Jing C. Tsai, Kaoshing; W. P. Chao, Hsinchu, all of Taiwan

[73] Assignee: Industrial Technology Research Institute, Hsinchu, Taiwan

[21] Appl. No.: 881,683

[22] Filed: Jun. 23, 1997

[51] Int. Cl.$^6$ ............................ C07F 17/00; C07F 7/00
[52] U.S. Cl. .................... 556/53; 546/3; 546/6; 546/7; 556/54; 556/56; 526/160; 526/943; 502/103; 502/117
[58] Field of Search .................. 556/53, 54, 56; 526/943, 160; 502/103, 117; 546/3, 6, 7

[56] References Cited

U.S. PATENT DOCUMENTS

| | | | |
|---|---|---|---|
| 3,505,369 | 4/1970 | Deffner | 260/429.5 |
| 5,279,999 | 1/1994 | DeBoer et al. | 502/117 |
| 5,670,680 | 9/1997 | Newman et al. | 556/53 |
| 5,723,398 | 3/1998 | Rosen et al. | 502/103 |

FOREIGN PATENT DOCUMENTS 0 655 467 A1  5/1995  European Pat. Off. .

OTHER PUBLICATIONS

Manzer, Journal of the American Chemical Society, vol. 100, No. 26, pp. 8068–8073, Dec. 1978.

*Primary Examiner*—Porfirio Nazario-Gonzalez
*Attorney, Agent, or Firm*—W. Wayne Liauh

[57] ABSTRACT

A novel trivalent Group IVB metal complex for preparing syndiotactic vinyl aromatic polymers is disclosed which is coordinated by a bidentate ligand and is represented by the formula (I):

$$(C_5R_nH_{5-n})M(BD)_mY_p \qquad (I)$$

wherein $C_5R_nH_{5-n}$ is a substituted or unsubstituted cyclopentadienyl group, n is an integer between 0 and 5, and R is $C_1$ to $C_{12}$ alkyl, aryl, substituted alkyl, or substituted aryl; M is a trivalent Group IVB metal; (BD) is a bidentate ligand with −1 valence, having a coordinating group which is capable of forming a coordinating bond or a chelating bond with the metal M; Y is selected from the group consisting of alkyl, aryl, aralkyl, halogen and hydrogen; m is an integer of 1 or 2; and m+p=2.

6 Claims, No Drawings

BIDENTATE COORDINATED TRIVALENT GROUP IVB METAL COMPLEX CATALYST FOR PREPARING SYNDIOTACTIC VINYL AROMATIC POLYMER

BACKGROUND OF THE INVENTION

1. Field of the Invention

The present invention relates to a novel bidentate coordinated trivalent Group IVB metal complex, and, more particularly, to a process for preparing syndiotactic vinyl aromatic polymers using the bidentate coordinated trivalent Group IVB metal complex as a catalyst.

2. Description of the Prior Art

Vinyl aromatic polymers, or vinyl aromatic compound-containing polymers in general, can be classified into three categories: atactic, isotactic, and syndiotactic. The vinyl aromatic polymers having a syndiotactic configuration have many advantageous properties than the atactic and isotactic counterparts. For example, syndiotactic polystyrenes exhibit the advantages of having high melting point (about 270° C.), low density (about 1.04 kg/cm$^3$), low dielectric constant (about 2.6), high vicat softening temperature (about 254° C.), excellent chemical resistance and water (steam) resistance, and low moisture absorption. The above reported values are measured from a specific syndiotactic polystyrene under a specific set of conditions. These values, of course, are subject to change as a result of different polymer molecular weight and many other factors.

In recent years, a trivalent titanium-based catalyst containing cyclopentadienyl as a ligand has been used for preparing syndiotactic vinyl aromatic polymers. For example, WO 95/10551 discloses a trivalent titanium-based catalyst composition for preparing syndiotactic vinyl aromatic polymers. Such catalyst composition includes pentamethylcyclopentadienyl titanium (III) dimethoxide [Cp*Ti(OMe)$_2$, in which Cp* represents pentamethylcyclopentadienyl and Me represents methyl], a borate, and a hydrocarbylation agent. In addition, European Patent No. 0,655,467 discloses the use of another trivalent titanium-based catalyst for preparing vinyl aromatic polymers.

However, the above-mentioned catalysts suffer from a number of shortcomings in that the catalyst has undesirable catalytic activity, inferior stereoselectivity, and the polymer so obtained exhibits an undesirably broad molecular weight distribution.

SUMMARY OF THE INVENTION

The primary object of the present invention is to solve the above-mentioned problems by providing a novel trivalent Group IVB metal complex for use in preparing vinyl aromatic polymers with high syndiotacticity. The trivalent Group IVB metal complex of the present invention is coordinated by a bidentate ligand with −1 (minus one) valence, such that the metal complex is stabilized by the coordinating or chelating bond between the trivalent Group IVB metal and the bidentate ligand. By using the bidentate coordinated Group IVB metal complex disclosed in the present invention as a catalyst for preparing vinyl aromatic polymers, the catalytic activity and stereoselectivity can be enhanced, and the polymer so produced has a narrower molecular weight distribution.

In the the present invention, a novel bidentate coordinated metal complex is disclosed which is represented by the following formula (I):

$$(C_5R_nH_{5-n})M(BD)_mY_p \quad (I)$$

wherein:

$C_5R_nH_{5-n}$ is a substituted or unsubstituted cyclopentadienyl group, n is an integer between 0 and 5, and R is $C_1$ to $C_{12}$ alkyl, aryl, substituted alkyl, or substituted aryl;

M is a trivalent Group IVB metal;

(BD) is a bidentate ligand with −1 valence, having a coordinating group which is capable of forming a coordinating bond or a chelating bond with the metal M;

Y is selected from the group consisting of alkyl, aryl, aralkyl, halogen and hydrogen;

m is an integer of 1 or 2; and m+p=2.

DETAILED DESCRIPTION OF THE INVENTION

The present invention discloses a novel bidentate coordinated metal complex which is represented by the following formula (I):

$$(C_5R_nH_{5-n})M(BD)_mY_p \quad (I)$$

wherein:

$C_5R_nH_{5-n}$ is a substituted or unsubstituted cyclopentadienyl group, n is an integer between 0 and 5, and R is $C_1$ to $C_{12}$ alkyl, aryl, substituted alkyl, or substituted aryl;

M is a trivalent Group IVB metal;

(BD) is a bidentate ligand with −1 valence, having a coordinating group which is capable of forming a coordinating bond or a chelating bond with the metal M;

Y is selected from the group consisting of alkyl, aryl, aralkyl, halogen and hydrogen;

m is an integer of 1 or 2; and m+p=2.

In a preferred embodiment of the present invention, the values of m and p are 2 and 0, respectively, and the metal complex is represented by $(C_5R_nH_{5-n})M(BD)_2$. In this embodiment, the bidentate coordinated metal complex of $(C_5R_nH_{5-n})M(BD)_2$ can be prepared by a process which includes the step of reacting $(C_5R_nH_{5-n})MCl_2$ with (BD)Li. The symbols R, n, M, and (BD) have the same definition as those described above.

As discussed above, the coordinating group contained in the bidentate ligand (BD) is capable of forming a coordinating bond or a chelating bond with the trivalent Group IVB metal M. The preferred embodiments of the coordinating group include nitrogen, phosphorus, oxygen, ether, or thioether.

Representative examples of the bidentate ligand (BD) includes:

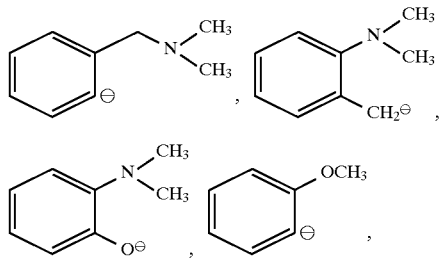

-continued

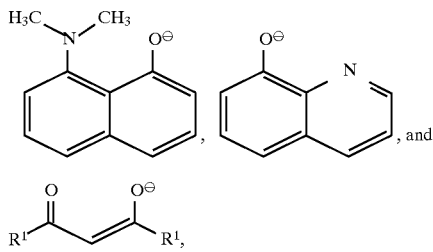

wherein R¹ is alkyl having from 1 to 6 carbon atoms. As defined earlier, M is a trivalent Group IVB metal, which can be titanium, zirconium, or hafnium, preferably titanium.

The group $C_5R_nH_{5-n}$ is a substituted or unsubstituted cyclopentadienyl group. Preferably $C_5R_nH_{5-n}$ is $\eta^5$-cyclopentadienyl or $\eta^5$-pentamethylcyclopentadienyl.

Representative examples of the bidentate coordinated metal complex of the present invention include:
($\eta^5$-C₅H₅)Ti(C₆H₄-o-CH₂NMe₂)₂;
($\eta^5$-C₅Me₅)Ti(C₆H₄-o-CH₂NMe₂)₂;
($\eta^5$-C₅H₅)Ti(CH₂C₆H₄-o-NMe₂)₂;
($\eta^5$-C₅Me₅)Ti(CH₂C₆H₄-o-NMe₂)₂;
($\eta^5$-C₅H₅)Ti(OC₆H₄-o-NMe₂)₂;
($\eta^5$-C₅Me₅)Ti(OC₆H₄-o-NMe₂)₂;
($\eta^5$-C₅H₅)Ti(C₆H₄-o-OCH₃)₂;
($\eta^5$-C₅Me₅)Ti(C₆H₄-o-OCH₃)₂;
($\eta^5$-C₅H₅)Ti(9-hydroxy-N,N-dimethyl-1-naphthylamine)₂;
($\eta^5$-C₅Me₅)Ti(9-hydroxy-N,N-dimethyl-1-naphthylamine)₂;
($\eta^5$-C₅H₅)Ti(8-hydroxyquinoline)₂;
($\eta^5$-C₅Me₅)Ti(8-hydroxyquinoline)₂;
($\eta^5$-C₅H₅)Ti(acetylacetone)₂; and
($\eta^5$-C₅Me₅)Ti(acetylacetone)₂;
wherein $\eta^5$-C₅H₅ represents a cyclopentadienyl group, Me represents a methyl group, and $\eta^5$-C₅Me₅ represents a pentamethylcylcopentadienyl group.

The bidentate coordinated metal complex of the present invention can be combined with an activating cocatalyst to form a catalyst composition, which can be used for preparing vinyl aromatic polymers with high syndiotacticity.

The activating cocatalyst can be methyl aluminoxane (MAO), a trialkyl aluminum, a dialkyl aluminum, a salt of an inert and non-coordinating anion, or a mixture thereof.

Preferably, the trialkyl aluminum is selected from the group consisting of trimethyl aluminum, triethyl aluminum, tripropyl aluminum, triisopropyl aluminum, tributyl aluminum, and triisobutyl aluminum (TIBA).

Preferably, the inert and non-coordinating anion is a borate. Examples of those borates that can be advantageously used in the present invention include N,N-dimethyl anilinium tetrakis(pentafluorophenyl)borate, triphenyl carbenium tetrakis(pentafluorophenyl)borate, trimethyl ammonium tetrakis(pentafluorophenyl)borate, ferrocenium tetrakis(pentafluorophenyl)borate, dimethyl ferrocenium tetrakis(pentafluorophenyl)borate, and silver tetrakis (pentafluorophenyl)borate.

Preferably, the activating cocatalyst is methyl aluminoxane, or a mixture of a trialkyl aluminum and a borate.

By using the catalyst composition of the present invention, which contains the novel bidentate coordinated metal complex of the present invention and an activating cocatalyst, syndiotactic vinyl aromatic polymers can be synthesized. One or more vinyl aromatic monomers can be subjected to polymerization in the presence of a catalytically effective amount of the catalyst composition of the present invention.

The suitable vinyl aromatic monomer can be represented by the formula (II):

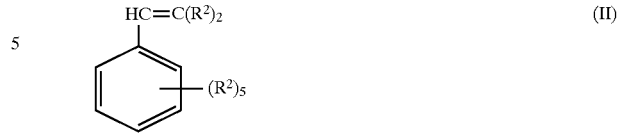

wherein each R² is independently selected from the group consisting of hydrogen; aliphatic, cycloaliphatic, aromatic hydrocarbon groups having from 1 to 10 carbon atoms; and halogen atoms. Examples of such monomers include styrene, chlorostyrene, n-butylstyrene, p-vinyltoluene, α-methylstyrene, etc., with styrene being especially suitable.

The present invention discloses a novel trivalent Group IVB metal complex, which can be used as a catalyst for preparing syndiotactic vinyl aromatic polymers. One of the key elements of the novel metal complex of the present invention, is that it contains a bidentate ligand with −1 valence, which is coordinated to the central trivalent Group IVB metal, such that the metal complex is stabilized by the coordinating or chelating bond between the trivalent Group IVB metal and the bidentate ligand. By using the bidentate coordinated Group IVB metal complex as a catalyst for preparing vinyl aromatic polymers, catalytic activity and stereoselectivity can be enhanced, and the polymer so obtained has a narrower molecular weight distribution than those obtained from the prior art processes.

The following examples are intended to more fully illustrate the process and the advantages of the present invention without limiting its scope, since numerous modifications and variations will be apparent to those skilled in the art.

EXAMPLE 1

Preparation of ($\eta^5$-C₅Me₅)Ti(C₆H₄-o-CH₂NMe₂)₂

1.27 g of [(C₅Me₅)TiCl₂]ₓ was charged into a 100 mL Schlenk flask, then 50 mL of ether was added and stirred. Thereafter, 1.41 g of (C₆H₄-o-CH₂NMe₂)Li was added slowly at 0° C., and the reddish green solution was quickly turned into reddish brown. The resulting solution was allowed to be in room temperature and the reaction was continued for about 5 hours. Finally the reaction solution was filtered to remove LiCl, and recrystallized in pentane to obtain 1.5 g of a dark red solid; yield 66%.

EXAMPLE 2

Preparation of ($\eta^5$-C₅H₅)Ti(C₆H₄-o-CH₂NMe₂)₂

The same procedures as described in Example 1 were employed except that the reactants were [($\eta^5$-C₅H₅)TiCl₂]ₓ (0.736 g, 4 mmol) and (C₆H₄-o-CH₂NMe₂)Li (1.13 g, 8 mmol). The final product was 0.88 g of a dark red solid; yield 58%.

EXAMPLE 3

Preparation of ($\eta^5$-C₅Me₅)Ti(CH₂C₆H₄-o-NMe₂)₂

The same procedures as described in Example 1 were employed except that (C₆H₄-o-CH₂NMe₂)Li was replaced by (CH₂C₆H₄-o-NMe₂)Li. The final product was a dark reddish brown solid; yield 60%.

EXAMPLE 4

Preparation of ($\eta^5$-C₅Me₅)Ti(8-hydroxyquinoline)₂

The same procedures as described in Example 1 were employed except that (C₆H₄-o-CH₂NMe₂)Li was replaced by two equivalents of 8-hydroxyquinoline lithium salt. The yield of the final product was 45%.

EXAMPLE 5

Preparation of $(\eta^5\text{-}C_5Me_5)Ti(acac)$

The same procedures as described in Example 1 were employed except that $(C_6H_4\text{-}o\text{-}CH_2NMe_2)Li$ was replaced by lithium salt of acetylacetone (acac), and ether was replaced by THF as the solvent. The reaction was conducted at room temperature for about 5 hours, and, after the reaction, the reaction solution was extracted and recrystallized in toluene to obtain a reddish brown solid.

EXAMPLE 6

Polymerization of Styrene

A mixture of 300 mL of an $Al_2O_3$-purified styrene monomer and 3.6 mL of a 10 wt % methylaluminoxane solution was placed in a 1-liter reactor. The reaction vessel was heated to 60° C. Then 0.0066 mmol of the catalyst obtained from Example 1 was added, and the reaction was conducted for 90 minutes. After the reaction was complete, the reaction product was washed with a hydrochloric acid/methanol mixture to decompose the catalyst component and dried to obtain 19 g of a resultant polymer, which was then subjected to Soxhlet extraction under boiling for 5 hours by the use of methyl ethyl ketone, 17.2 g of the insoluble component was obtained. For this resultant syndiotactic polymer, the weight average molecular weight was 2,630,000; the number molecular weight was 1,310,000 and in its thermal differential analysis, the melting point was 271° C.

EXAMPLES 7–10

The same procedures described in Example 6 for preparing syndiotactic polystyrene were employed except that the catalysts used were respectively replaced by the catalysts obtained from Examples 2–5. The syndiotactic polystyrene obtained from Example 7 was analyzed to have a weight average molecular weight of 184,000, a number molecular weight of 98,000, and a molecular weight distribution of 1.87. The other results were shown in Table 1.

COMPARATIVE EXAMPLE 1

The same procedures described in Example 6 for preparing syndiotactic polystyrene were employed except that the catalyst used was replaced by pentamethylcyclopentadienyl titanium (III) dimethoxide $Cp^*Ti(OMe)_2$. The results were shown in Table 1.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

TABLE 1

| Example | Catalyst | Catalyst amount (mmol) | MAO amount (mL) | Reaction time (minutes) | Catalytic activity (g – sPS/g – Ti · h) | Melting point (°C.) |
| --- | --- | --- | --- | --- | --- | --- |
| 6 | Example 1 | 0.0066 | 3.6 | 90 | $4 \times 10^4$ | 271 |
| 7 | Example 2 | 0.0065 | 3.6 | 90 | $7.2 \times 10^4$ | 254 |
| 8 | Example 3 | 0.0044 | 2.4 | 60 | $3.1 \times 10^4$ | 267 |
| 9 | Example 4 | 0.0067 | 3.6 | 90 | $5.5 \times 10^3$ | — |
| 10 | Example 5 | 0.0067 | 3.6 | 60 | $4.3 \times 10^3$ | — |
| Comparative | $Cp^*Ti(OMe)_2$ | 0.0044 | 2.4 | 60 | $1.3 \times 10^4$ | 266 |

What is claimed is:

1. A bidentate coordinated metal complex represented by the following formula (I):

$$(C_5R_nH_{5-n})M(BD)_mY_p \qquad (I)$$

wherein:

$C_5R_nH_{5-n}$ is a substituted or unsubstituted cyclopentadienyl group, n is an integer between 0 and 5, and R is a $C_1$ to $C_{12}$ alky, aryl, substituted alkyl, or substituted aryl;

M is a trivalent Group IVB metal;

(BD) is a bidentate ligand with a −1 valence, selected from the group consisting of

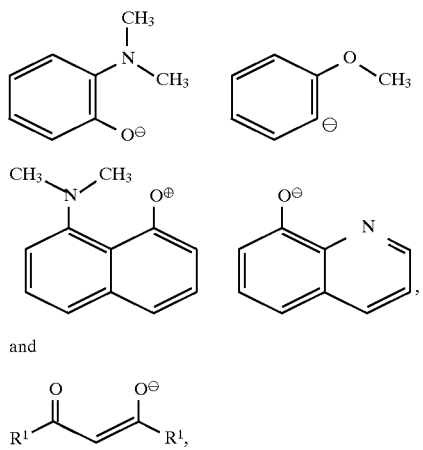

and wherein $R^1$ is alkyl having from 1 to 6 carbons atoms;

Y is selected from the group consisting of alkyl, aryl, aralkyl, halogen, and hydrogen;

m is an integer of 1 or 2; and m+p=2.

2. The metal complex as claimed in claim 1, wherein the coordinating group contained in the bidentate ligand (BD) is selected from the group consisting of nitrogen, phosphorus, oxygen, ether, and thioether.

3. The metal complex as claimed in claim 1, wherein the metal M is selected from the group consisting of titanium, zirconium, and hafnium.

4. The metal complex as claimed in claim 1, wherein the metal M is titanium.

5. The metal complex as claimed in claim 1, wherein the $C_5R_nH_{5-n}$ is selected from the group consisting of $\eta^5$-cyclopentadienyl and $\eta^5$-pentamethylcyclopentadienyl.

6. The metal complex as claimed in claim 1 which is represented by one of the formulas selected from the group consisting of:

$(\eta^5-C_5H_5)Ti(OC_6H_4-o-NMe_2)_2$;
$(\eta^5-C_5Me_5)Ti(OC_6H_4-o-NMe_2)_2$;
$(\eta^5-C_5H_5)Ti(C_6H_4-o-OCH_3)_2$;
$(\eta^5-C_5Me_5)Ti(C_6H_4-o-OCH_3)_2$;
$(\eta^5-C_5H_5)Ti(9\text{-hydroxy-}N,N\text{-dimethyl-1-naphthylamine})_2$;
$(\eta^5-C_5Me_5)Ti(9\text{-hydroxy-}N,N\text{-dimethyl-1-naphthylamine})_2$;
$(\eta^5-C_5H_5)Ti(8\text{-hydroxyquinoline})_2$;
$(\eta^5-C_5Me_5)Ti(8\text{-hydroxyquinoline})_2$;
$(\eta^5-C_5H_5)Ti(\text{acetylacetone})_2$; and
$(\eta^5-C_5Me_5)Ti(\text{acetylacetone})_2$;
wherein $\eta^5-C_5H_5$ represents a cyclopentadienyl group, Me represents a methyl group, and $\eta^5-C_5Me_5$ represents a pentamethylcylcopentadienyl group.

* * * * *